United States Patent
Li et al.

(10) Patent No.: US 11,911,460 B1
(45) Date of Patent: Feb. 27, 2024

(54) LIPID DELIVERY SYSTEM AND VIRUS-LIKE STRUCTURE (VLS) VACCINE CONSTRUCTED THEREFROM

(71) Applicants: Weirui Biotechnology (Kunming) Co., LTD., Kunming (CN); Shandong Weigao Litong Biological Products Co., Ltd., Weihai (CN)

(72) Inventors: Qihan Li, Kunming (CN); Kaili Ma, Kunming (CN); Yanmei Li, Kunming (CN); Jingjing Zhang, Kunming (CN); Lichun Wang, Kunming (CN); Changyong Mu, Kunming (CN); Xiaowu Peng, Kunming (CN); Yanrui Su, Kunming (CN); Chang'e Liu, Kunming (CN); Liping He, Kunming (CN); Lin Feng, Kunming (CN); Dongxiu Gao, Kunming (CN); An Wang, Kunming (CN); Hongbing Li, Kunming (CN); Gang Xu, Kunming (CN); Fuyun He, Kunming (CN); Lichun Zheng, Kunming (CN); Hongkun Yi, Kunming (CN)

(73) Assignees: Weirui Biotechnology (Kunming) Co., LTD., Kunming (CN); Shandong Weigao Litong Biological Products Co., Ltd., Weihai (CN)

( * ) Notice: Subject to any disclaimer, the term of this patent is extended or adjusted under 35 U.S.C. 154(b) by 0 days.

(21) Appl. No.: 18/228,700

(22) Filed: Aug. 1, 2023

(30) Foreign Application Priority Data

Apr. 23, 2023 (CN) .......................... 202310436870.2

(51) Int. Cl.
*A61K 39/215* (2006.01)
*A61P 37/04* (2006.01)
*A61K 39/00* (2006.01)

(52) U.S. Cl.
CPC ............ *A61K 39/215* (2013.01); *A61P 37/04* (2018.01); *A61K 2039/53* (2013.01); *A61K 2039/55555* (2013.01)

(58) Field of Classification Search
None
See application file for complete search history.

(56) References Cited

FOREIGN PATENT DOCUMENTS

WO    WO 2021/142336    *    7/2021

OTHER PUBLICATIONS

Doetze et al. (International Immunology. 1997; 9 (5): 721-729).*
Glebe et al. (Journal of Virology. 2003; 77 (17): 9511-9521).*

* cited by examiner

*Primary Examiner* — Shanon A. Foley
(74) *Attorney, Agent, or Firm* — Bayramoglu Law Offices LLC (57) ABSTRACT

A lipid delivery system, a virus-like structure (VLS) vaccine constructed therefrom, and a lipid particle capable of encapsulating an mRNA molecule encoding a SARS-CoV-2-specific antigen are provided. After the lipid particle encapsulates an mRNA molecule encoding a SARS-CoV-2 antigen, a SARS-CoV-2 S1 antigen protein can be embedded on a surface of an envelope structure of the lipid under specific buffer conditions to produce a VLS vaccine with an antigen-encoding mRNA molecule encapsulated inside and an outer membrane presenting a required viral antigen protein. The vaccine has a superior specific antibody-inducing ability to a SARS-CoV-2 mRNA vaccine and a polypeptide vaccine, can maintain a long-lasting high antibody level, and can also exhibit excellent immune binding abilities for the emerging different variants.

4 Claims, 5 Drawing Sheets
(2 of 5 Drawing Sheet(s) Filed in Color)

Muscle (immune site)

FIG. 8A

Lymph node

FIG. 8B

Spleen

FIG. 8C

Blank

FIG. 9A

VLS

FIG. 9B mRNA

FIG. 9C

LIPID DELIVERY SYSTEM AND VIRUS-LIKE STRUCTURE (VLS) VACCINE CONSTRUCTED THEREFROM

CROSS REFERENCE TO THE RELATED APPLICATIONS

This application is based upon and claims priority to Chinese Patent Application No. 2023104368702, filed on Apr. 23, 2023, the entire contents of which are incorporated herein by reference.

TECHNICAL FIELD

The present disclosure belongs to the technical field of biomedicine, and in particular relates to a lipid nanoparticle (LNP), a lipid delivery system, and a virus-like structure (VLS) vaccine.

BACKGROUND

In the development of vaccines against diseases caused by infection of the emerging novel coronavirus (SARS-CoV-2), the successful application of a novel mRNA vaccine with a specific LNP as a carrier suggests that a sac-like structure formed by lipid molecules under specific physicochemical conditions can be fused with a lipid structure of a cell membrane, which makes it possible to directly deliver an mRNA molecule encoding an antigen into a cell and translate the mRNA molecule into an antigen protein. This technical breakthrough not only provides a new idea for the research and development of vaccines against the virus SARS-CoV-2, but also lays a technical foundation for the research of novel SARS-CoV-2 vaccines in other forms.

A process of delivering an mRNA molecule in an LNP mode is similar to a process of naturally infecting a cell by the virus SARS-CoV-2 to some degree, and a main difference between the two processes is as follows: a specific membrane protein (spike protein, S1 protein) on a surface of an envelope of the virus SARS-CoV-2 usually binds to a specific protein receptor (ACE2 receptor) on a respiratory cell membrane to make an envelope of the virus close to the cell membrane and make the two lipid membranes fused with each other, such that a gene (negative-strand RNA) of the virus enters the cell to start an infection process.

Currently, there are many types of LNP-based mRNA vaccines, but it is still of positive significance for acquisition of a superior vaccine with a long antibody maintenance time.

In addition, cholesterol is one of the essential components of the current LNP and is intended to play a role of a stabilizing agent.

SUMMARY

Structural biology studies of different enveloped viruses also show that a glycoprotein (GP) encoded by a virus in a cell is usually secreted onto a cell membrane through an endoplast in a suitable pH environment, and then is encapsulated by a cell lipid membrane with an outer membrane protein of the virus when a virus nucleocapsid particle exits the membrane to finally produce a complete viral particle. Based on structural and biological characteristics of SARS-CoV-2 and physicochemical characteristics of a lipid particle of an mRNA delivery system, the present disclosure designs and develops a lipid particle that can encapsulate an mRNA molecule encoding a SARS-CoV-2-specific antigen, where a cationic lipid molecule ((2-(2-hydroxyethoxy)ethyl) azanediyl)bis(hexane-6,1-diyl)bis(2-hexyldecanoate) (DHA-1) produced in China, a polyethylene glycol (PEG)-lipid molecule methoxypoly(ethylene glycol)-N-tetradecyltetradecanamide-2K (mPEG-DTA-1-2K) produced in China, a commercial cationic lipid (2,3-dioleoyl-propyl)-trimethylammonium-chloride (DOTAP), and a phospholipid molecule 1,2-dioleoyl-SN-glycero-3-phosphocholine (DOPC) are formulated according to a specific ratio and the lipid particle is prepared by microfluidic device under specific buffer conditions. After the lipid particle encapsulates an mRNA molecule encoding a SARS-CoV-2 antigen, a SARS-CoV-2 S1 antigen protein can be embedded on a surface of an envelope structure of the lipid particle under specific buffer conditions to produce a VLS vaccine with an antigen-encoding mRNA molecule encapsulated inside and an outer membrane presenting a required viral antigen protein. Molecular biology analysis and immunology analysis show that the LNP-based VLS vaccine has a superior specific antibody-inducing ability to a SARS-CoV-2 mRNA vaccine and a polypeptide vaccine, can maintain a long-lasting high antibody level, and can also exhibit excellent immune binding abilities for the emerging different variants.

To achieve the above objective, the present disclosure provides an LNP, a delivery system including the LNP, and a preparation method of a VLS vaccine in which an mRNA molecule is encapsulated by the LNP and an antigen protein molecule binds to a surface of the lipid particle membrane.

The LNP Includes:
cationic lipid: DHA-1;
cationic lipid: DOTAP;
neutral phospholipid molecule: DOPC; and
PEGylated lipid molecule: mPEG-DTA-1-2K.

The DHA-1 and the mPEG-DTA-1-2K are domestic products in China, and both are produced by the Xiamen Sinopeg Biotech co., Ltd.

Further, the DHA-1, the DOTAP, the DOPC, and the mPEG-DTA-1-2K are in a molar ratio of (10-13):(27-29):(56-59):(1.6-1.9).

The delivery system includes the LNP.

Further, the delivery system has a pH of 6.2 to 6.8.

Further, the delivery system adopts a buffer including 10 mM NaAc, and 0.0001% (w/v) trehalose (Hereinafter referred to as buffer D).

The lipid system is used in preparation of a VLS vaccine, where an mRNA molecule is encapsulated by the lipid system and a protein molecule binds to a surface of the lipid particle.

The VLS vaccine includes mRNA and the delivery system.

Further, in the VLS vaccine, the delivery lipid particle encapsulates mRNA, and a protein molecule binds to a surface of the lipid particle.

Further, in the VLS vaccine, the encapsulated mRNA is an S1 protein-encoding gene of an Omicron XBB.1 virus strain; and the protein molecule binding to the surface of the delivery lipid particle is an S1 antigen that is encoded by the Omicron BA.1 virus strain and is expressed in a Chinese hamster ovary (CHO) cell and purified by chromatography.

A preparation method of the VLS vaccine is provided, including the following steps:
(1) mixing the DHA-1, the DOTAP, the DOPC, and the mPEG-DTA-1-2K dissolved in absolute ethanol according to a molar ratio of (10-13):(27-29):(56-59):(1.6-1.9); and diluting mRNA with buffer D;
(2) encapsulating an mRNA molecule by a microfluidic technology to produce an mRNA-LNP system;

(3) diluting the mRNA-LNP system obtained in step (2) with buffer D in a volume 30 times a volume of the mRNA-LNP system, and subjecting a resulting diluted system to ultrafiltration (UF) concentration with a 100 Kda UF membrane to obtain an mRNA-LNP ethanol free system and a nitrogen-phosphorus molar ratio of (4-6):1;

(4) using 500 mM HAC to adjust a pH of the mRNA-LNP ethanol free system to 6.2 to 6.8;

(5) adding the S1 antigen protein expressed in the CHO cell and purified by chromatography to a buffer D with a pH of 6.2 to 6.8 to prepare a protein preparation solution for the VLS vaccine; and (6) mixing an mRNA-LNP system obtained in step (4) with a protein system obtained in step (5), and subjecting a resulting mixed system to mild rotary-mixing at room temperature for 30 min, then staying overnight at 4° C. to obtain a virus-like-structure vaccine system, which is a stock solution for the VLS vaccine; and according to dose setting requirements (specifically: mRNA/protein: 200-250 μg/50-60 μg), diluting the stock solution to a corresponding volume with a buffer including 20 mM NaAc, 0.01 (w/v) trehalose, and 3.5% sucrose (a specific volume is determined according to a scale of a production batch) to obtain a working solution for the VLS vaccine.

The present disclosure has the following beneficial effects:

The LNP of the present disclosure can encapsulate an mRNA molecule encoding a SARS-CoV-2-specific antigen (an S1 protein-encoding gene of an Omicron XBB.1 virus strain). After the LNP encapsulates an mRNA molecule, a SARS-CoV-2 S1 antigen protein (an S1 protein of the Omicron BA.1 virus strain) can be embedded on a surface of an envelope structure of the lipid particle under specific buffer conditions to produce a VLS vaccine with an antigen-encoding mRNA molecule encapsulated inside and an outer membrane presenting a required viral antigen protein. The vaccine has a superior specific antibody-inducing ability to a SARS-CoV-2 mRNA vaccine and a polypeptide vaccine, can maintain a long-lasting high antibody level, can lead to an antibody exhibiting excellent immune binding abilities for the emerging different variants, and has excellent safety.

The formula of the LNP of the present disclosure does not require the use of cholesterol as a stabilizing agent, can allow excellent stability through a specific ratio of two cationic lipids, and can allow a prominent carrier delivery effect. A delivery system constructed with the LNP of the present disclosure as a carrier does not require cholesterol as a stabilizing agent, and can lead to an encapsulation rate of 92% to 95% for an mRNA molecule.

Further, the cationic lipid DHA-1 and PEGylated lipid molecule used in the present disclosure are domestic products in China.

BRIEF DESCRIPTION OF THE DRAWINGS

The application file contains at least one drawing executed in color. Copies of this patent or patent application publication with color drawing(s) will be provided by the Office upon request and payment of the necessary fee.

Notes: In FIGS. 1A-1C, FIG. 1A shows the VLS particles of the present disclosure that encapsulate an mRNA molecule and include an antigen protein molecule binding to a surface of the particles; FIG. 1B shows the mRNA-LNP particles that are not loaded with a protein and only encapsulate an mRNA molecule; and FIG. 1C shows the LNP particles that does not encapsulate an mRNA molecule and is not loaded with an antigen protein.

In FIG. 3 and FIG. 4, M represent a marker, 1 represents a control eluate, 2 represents an mRNA eluate (mRNA), 3 represents a VLS eluate (Sample), 4 represents a control supernate (control-supernate), and 5 represents an mRNA supernate (mRNA-supernate).

In FIGS. 5A-5B, FIG. 5A shows immunofluorescence (IF) detection results of different cells transfected with VLS that encapsulates an EGFP protein-encoding mRNA molecule and includes an S1 antigen protein binding to a surface of the lipid particle; and FIG. 5B shows WB detection results of these cells transfected with VLS that encapsulates an S1 protein-encoding mRNA molecule and includes an S1 antigen protein binding to a surface of the lipid particle, where M represents a marker.

In FIGS. 6A-6C, FIG. 6A shows binding antibody titers against WT, Omicron and Delta strains by different vaccine systems, and FIG. 6B shows the neutralizing antibody titers against WT, Omicron and Delta strains with pseudoviral neutralizing antibody detection systems by different vaccine systems. FIG. 6C shows the neutralizing antibody titers against Omicron strain in Vero cells In FIGS. 9A-9C, an arrow indicates an aggregation site of inflammatory cells, with a scale of 100 μm.

DETAILED DESCRIPTION OF THE EMBODIMENTS

In order to make the objectives, technical solutions, and beneficial effects of the present disclosure clear, the technical solutions of the present disclosure will be described in detail below. Apparently, the described embodiments are merely some rather than all of the embodiments of the present disclosure. All other embodiments obtained by those skilled in the art based on the embodiments of the present disclosure without creative efforts should fall within the protection scope of the present disclosure.

The present disclosure provides an LNP, including the following four components:

cationic lipid produced in China: DHA-1;

cationic lipid: DOTAP; neutral phospholipid molecule: DOPC; and

PEGylated lipid molecule produced in China: mPEG-DTA-1-2K.

The DHA-1, the DOTAP, the DOPC, and the mPEG-DTA-1-2K are in a molar ratio of (10-13):(27-29):(56-59):(1.6-1.9).

The present disclosure also provides a preparation method of a lipid delivery system and a VLS vaccine, including the following steps:

(1) The DHA-1, DOTAP, DOPC, and mPEG-DTA-1-2K are dissolved in absolute ethanol respectively the present disclosure, then are mixed according to a molar ratio of (10-13):(27-29):(56-59):(1.6-1.9); and mRNA is diluted with buffer D.

(2) A microfluidic device (NanoAssemblr® Ignite™ Model) is used to prepare an mRNA-LNP system according to the following specific parameters: FRR: 1:3, TFR: 20 mL/min, and waste vol: 0.65+0.05 mL.

(3) The mRNA-LNP system obtained in step (2) is diluted with buffer D in a volume 30 times a volume of the mRNA-LNP system, and a resulting diluted system is subjected to UF concentration with a 100 Kda UF membrane to obtain an mRNA-LNP ethanol free system and a nitrogen-phosphorus molar ratio of (4-6):1, which is a preparation solution for a VLS vaccine.

(4) 500 mM HAC is used to adjust a pH of the mRNA-LNP ethanol free system to 6.2 to 6.8.

(5) AN S1 protein of a SARS-CoV-2 Omicron BA.1 virus strain that is expressed in a CHO cell and purified by chromatography is added to a buffer D with a pH of 6.2 to 6.8 to prepare a protein preparation solution for the VLS vaccine.

(6) an mRNA-LNP ethanol free system obtained in step (4) is mixed with a protein system obtained in step (5), and a resulting mixed system is subjected to mild rotary-mixing at room temperature for 30 min and then to staying overnight at 4° C. to obtain a virus-like structure vaccine system (referred to as VLS system), which is a stock solution for the VLS vaccine.

Example 1

A stock solution for a VLS vaccine was prepared with DHA-1, DOTAP, DOPC, and mPEG-DTA-1-2K in a molar ratio of 10:27:59:1.6 and buffer D at a pH of 6.2 according to the above method.

Characteristic Analysis of a VLS System:

The previous analysis for an LNP system for an mRNA vaccine mainly involves a variety of physicochemical parameters of LNPs, such as particle size, zeta potential, and polymer dispersion index. A VLS system also adopts a LNP as a main carrier, and thus when encapsulating/embedded with an mRNA/protein molecule, the carrier exhibits corresponding physicochemical characteristics. When the lipid carrier does not encapsulate an mRNA molecule and is not embedded with a protein, the lipid carrier has a particle size of about 50 nm to 60 nm (Table 1). After the lipid carrier encapsulates an mRNA by the microfluidic technology described in Example 1, the particle size is about 70 nm to 100 nm; and after the lipid carrier is further loaded with an antigen protein, the particle size of the lipid carrier increases to 100 nm to 110 nm. In addition, with the encapsulation of the mRNA and the loading of the protein, a zeta potential of the lipid carrier decreases accordingly in a range merely of 40 mv to 25 mv. An encapsulation rate of the lipid system for the mRNA molecule was detected to be 92% to 95% (as shown in Table 1).

TABLE 1

Physicochemical characteristic analysis of the VLS system

| Status | Size (nm) | PDI | Zeta (mV) | Encapsulation rate |
|---|---|---|---|---|
| No encapsulation | 57.71 ± 3.66 | 0.20 ± 0.01 | 33 ± 4.76 | — |
| Encapsulating mRNA molecule | 81.41 ± 4.12 | 0.19 ± 0.01 | 34.5 ± 12.74 | 95.7% |
| Encapsulating mRNA molecule and loaded with an antigen protein | 114.99 ± 2.54 | 0.16 ± 0.02 | 32.97 ± 1.03 | 93.8% |

Figure 1A:
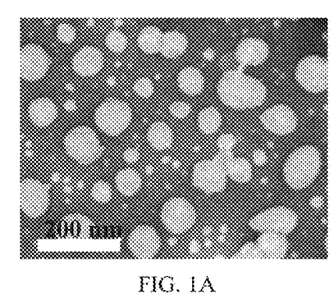
FIGS. 1A-1C show electron microscopy (EM) images of VLS, mRNA-LNP, LNP of Example 1 of the present disclosure.
Figure 1B:
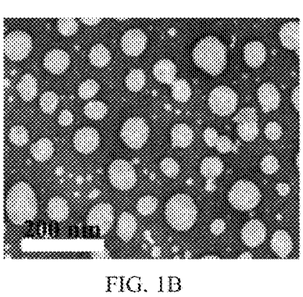
Figure 1C:
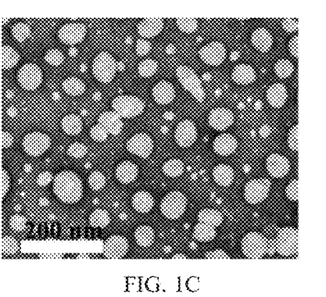

Structural biology observations of viruses with envelopes suggest that these viruses usually refer to viruses in which a viral DNA/RNA strand-containing nucleocapsid structure is encapsulated by a same lipid membrane and a viral surface GP is usually present on a lipid membrane. The VLS system of the present disclosure refers to a system in which a corresponding antigen protein is embedded on a lipid membrane encapsulating an mRNA molecule, and this characteristic is first manifested in particularity of a structure of the system. EM observations show that, in the VLS system of the present disclosure, VLS particles are spherical and have coronal protrusions on their surfaces; and the VLS system of the present disclosure is obviously different from an LNP that is not loaded with a protein, only encapsulates an mRNA molecule, and an empty-shell structure that does not encapsulate an mRNA molecule and is not loaded with an antigen protein (FIGS. 1A-IC).

Figure 2:
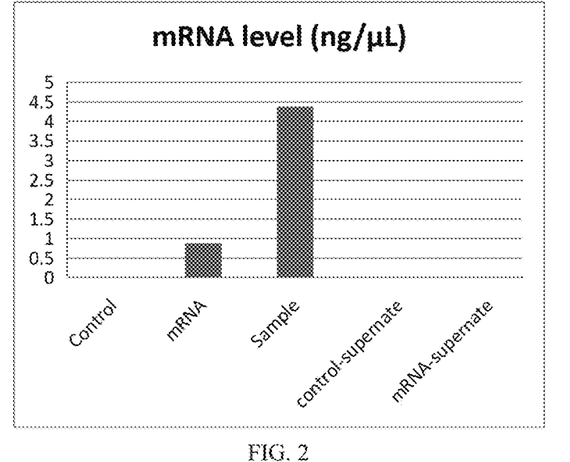
FIG. 2 shows Q-RT-PCR detection results of an antigen protein encapsulated by the VLS of Example 1 of the present disclosure.
Figure 3:
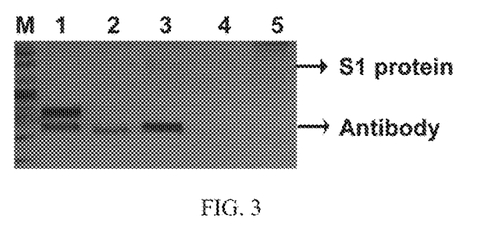
FIG. 3 shows PAGE-silver staining results of an antigen protein encapsulated by the VLS system of Example 1 of the present disclosure.
Figure 4:
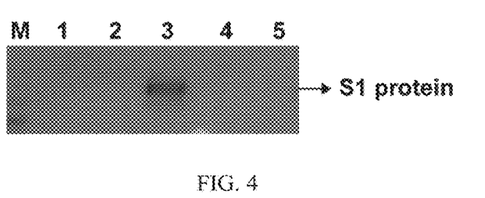
FIG. 4 shows Western blotting (WB) detection results of an antigen protein encapsulated by the VLS system of Example 1 of the present disclosure.

Verification of the characteristic of the VLS system to encapsulate an mRNA molecule and be loaded with an antigen protein:

In order to confirm the characteristic of the VLS system to encapsulate an mRNA molecule and be loaded with an antigen protein, with a co-immunoprecipitation method, the VLS particle is allowed to bind to an anti-S antigen specific antibody, then the antibody is allowed to bind to a *Staphylococcus aureus* (*S. aureus*) protein A-adsorbed magnetic bead, and a resulting product is incubated and washed to obtain purified VLS; and the purified VLS was subjected to electrophoresis-silver staining analysis (test results were shown in FIG. 3) and WB analysis, and the VLS captured by the anti-S protein specific antibody was subjected to a specific q-RT-PCR test for a S gene. Results show that the VLS particle specifically captured by the anti-S protein antibody can be detected by q-RT-PCR for the lipid particle-encapsulated S gene, indicating that the particle includes an mRNA molecule (FIG. 2). WB results also indicate the presence of the S antigen protein in the particle (FIG. 4). These results confirm from the perspectives of both a morphology and a particle composition that the lipid particle is a VLS structure in which an mRNA molecule is encapsulated and an antigen protein is embedded on a surface of a lipid membrane. A specific detection method was as follows: A mouse antibody with a high anti-S1 antibody titer (GMT>1024000) was added to each of the prepared VLS experimental vaccine, an mRNA vaccine, and a blank delivery system (in a volume ratio: 1:100, where a volume of the mouse antibody was 1), and resulting mixtures each were mixed and incubated overnight at 4° C.; then 50 μL of a Suzhou BEAVER Protein A/G magnetic bead treated with a buffer (Tris-HCL: 10 mM; NaCl: 20 mM; KCl: 2.5 mM; and NP-40: 0.1%) was added to each sample, and a resulting mixture was incubated at room temperature for 30 min; and the magnetic bead was adsorbed by a magnetic pole, washed with a buffer (Tris-HCL: 10 mM; NaCl: 50 mM; KCl: 2.5 mM; and NP-40: 0.1%) 2 to 3 times, and then subjected to elution. A solution obtained after the magnetic bead separation and a solution obtained after the elution each were subjected to a q-RT-PCR test, an S1 mRNA copy number test, and WB and SDS-PAGE-silver staining analysis for qualitative detection of an S1 protein.

Figure 5A:
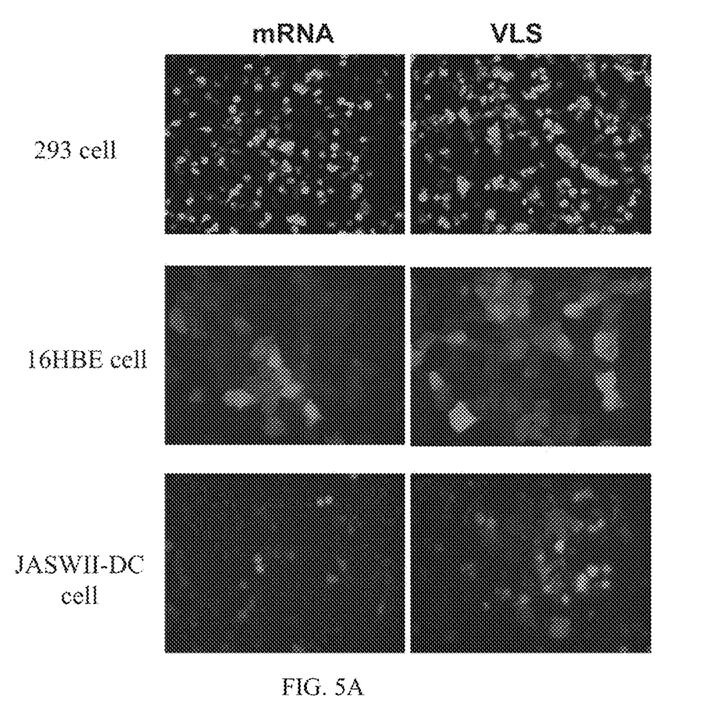
FIGS. 5A-5B show transfection abilities of the VLS system of Example 1 of the present disclosure for cells.
Figure 5B:
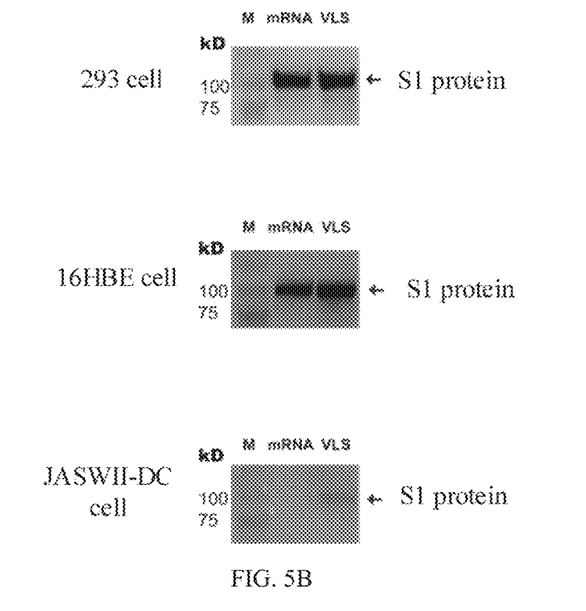

Verification of a transfection ability of the VLS system and a binding ability of the VLS system to a cellular ACE2 receptor:

Since a main delivery ability of VLS was based on a liposome that could be fused with a cell, a transfection ability of the VLS experimental vaccine and a binding ability of the VLS experimental vaccine to the cell ACE2 receptor were verified. Results showed that, in a 293 cell for which a conventional liposome (a commercial lipofectine reagent) exhibited an excellent transfection effect, the VLS experimental vaccine could produce a prominent transfection effect (FIG. 5A); and in a 16HBE cell and a dendritic cell (DC) for which a common liposome exhibited poor transfection efficiency, because the VLS system could bind to ACE2 receptors on surfaces of these cells, the VLS system exhibited high transfection efficiency, which was higher than the transfection efficiency of the commonly-used lipofectine (FIG. 5A). This is reflected not only in the use of a fluorescent protein-encoding mRNA, but also in a WB test result of an anti-S antigen specific antibody obtained after transfection by the S1 gene (FIG. 5B).

Immunological characteristics of the VLS experimental vaccine:

The immunological efficiency of the VLS experimental vaccine was tested with Balb/c mice and ACE transgenic mice: Balb/C mice were immunized through intramuscular injection according to a day 0-day 21 immunization program; on day 21 after primary immunization and day 14 and day 28 after booster immunization, blood was collected from a tail vein, and serum was isolated from the blood and tested for a binding antibody and a neutralizing antibody; and on day 28 after booster immunization, a spleen was collected, and mouse lymphocytes were isolated and subjected to enzyme-linked immunospot (ELISpot) assay to detect a cellular immune response.

The binding antibody was subjected to parallel detection with anti-WT, Delta, and Omicron strain Elisa kits.

The neutralizing antibody was tested with anti-WT, Delta, and Omicron strain pseudoviral neutralizing antibody detection systems, and tested with a Vero cell system for an Omicron strain.

Figure 6A:
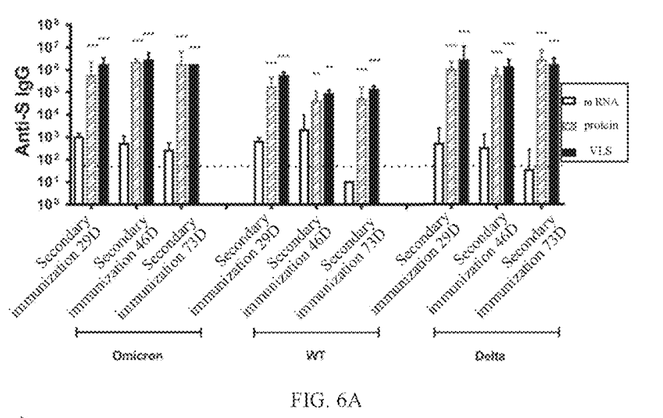
FIGS. 6A-6C show immunological characteristics of different vaccine systems of Example 1 of the present disclosure.
Figure 6B:
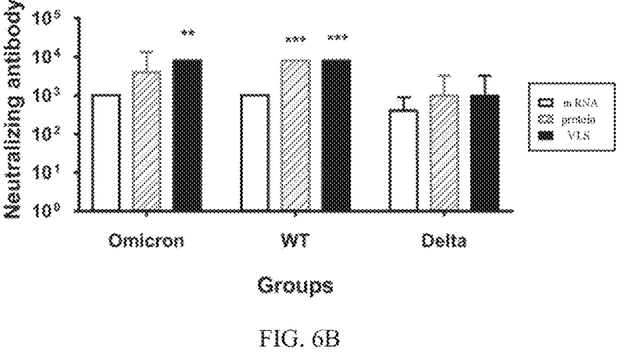
Figure 6C:
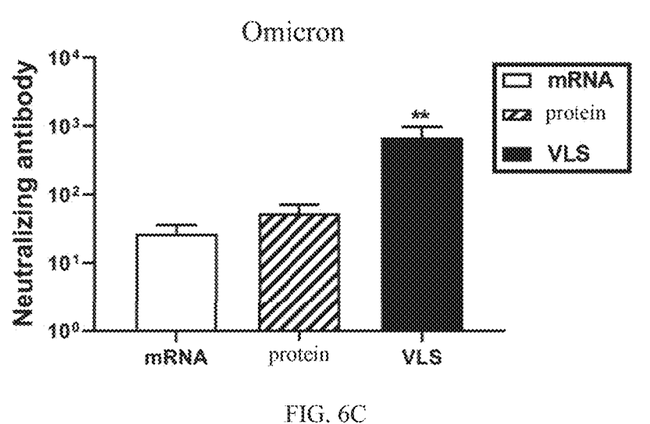
Figure 7A:
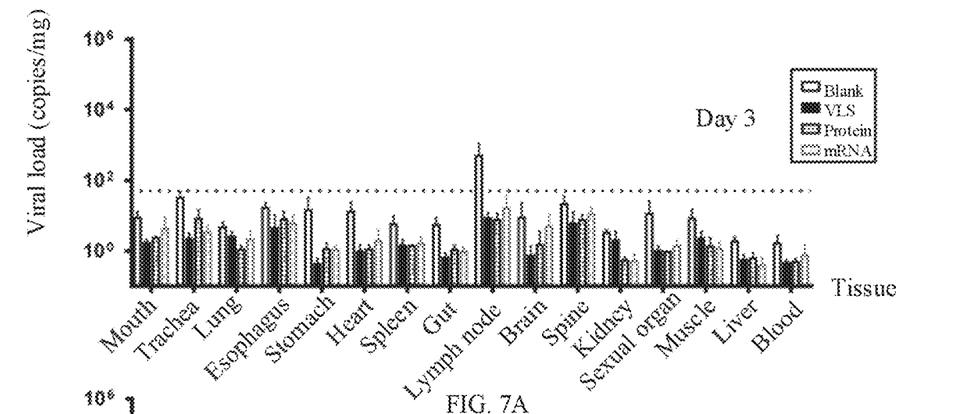
FIGS. 7A-7C show viral loads of different vaccine systems of Example 1 of the present disclosure in different tissues of mice.
Figure 7B:
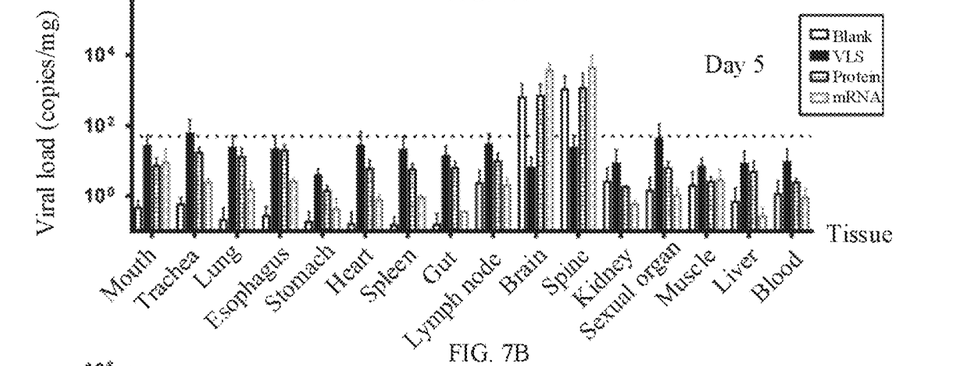
Figure 7C:
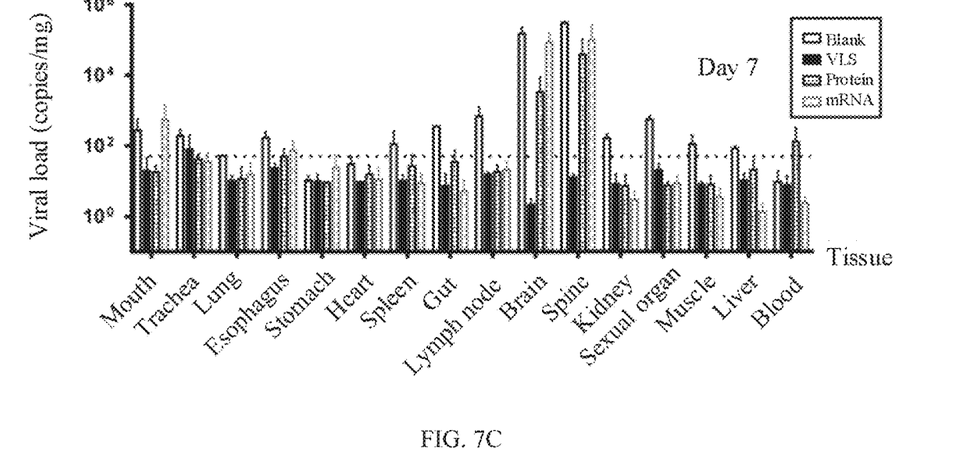

Results: After a same immunization program (day 0, day 21) at a same dose, the VLS experimental vaccine leaded to a binding antibody and a neutralizing antibody with significant advantages compared with an mRNA vaccine and a polypeptide vaccine (FIGS. 6A-6C), and maintenance times of these antibodies were significantly longer than that of the mRNA vaccine and the polypeptide vaccine. Three months after booster immunization, antibodies induced by the mRNA vaccine and the polypeptide vaccine were decreased significantly, but the binding antibody induced by the VLS experimental vaccine of the present disclosure was still maintained at a titer of $10^{6-7}$ or higher (FIG. 6A), and the neutralizing antibody induced by the VLS experimental vaccine of the present disclosure was still maintained at a titer of about $10^3$ (FIGS. 6B-6C). More importantly, when attacked by an Omicron virus strain, $ACE^{+/+}$ mice immunized with the VLS experimental vaccine completely avoided the proliferative infection of the virus in vivo (FIGS. 7A-7C); and although the mRNA vaccine and the polypeptide vaccine exhibited protective effects for the mice, test results of viral loads in tissues and organs indicated that these mice did not completely block the proliferative infection of the virus in vivo (FIGS. 7A-7C).

The above experimental results confirmed the preclinical analysis results of the SARS-CoV-2 VLS experimental vaccine and the superior immunological effects of the SARS-CoV-2 VLS experimental vaccine in the animal experiment to the SARS-CoV-2 mRNA and polypeptide vaccines.

Safety observation of the VLS experimental vaccine:

For an LNP that completely adopts lipid products produced in China and a proprietary formula and a VLS experimental vaccine constructed with the LNP, the safety evaluation for the LNP and the VLS experimental vaccine based on their immune effectiveness is very important. Based on the characteristics of a lipid delivery system, the safety of the VLS experimental vaccine was investigated in the following aspects.

Based on the background that the VLS could bind to cells with ACE2 receptors in different tissues because a surface of an envelope of the VLS was embedded with an S1 protein of SARS-CoV-2, transgenic mice with ACE2 receptors were used to investigate the distribution of the VLS experimental vaccine with a fluorescent protein-encoding gene mRNA encapsulated and an S1 protein embedded on a surface of a lipid membrane in major organs and tissues in vivo after immunization.

Figure 8A:
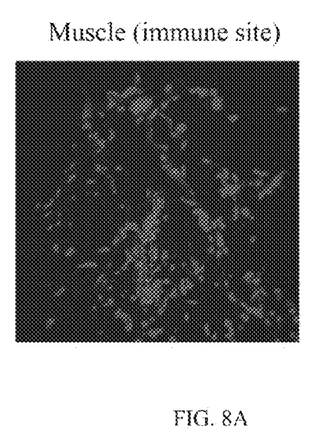
FIGS. 8A-8C show the distribution of the immune VLS experimental vaccine of Example 1 of the present disclosure in tissues and organs.
Figure 8B:
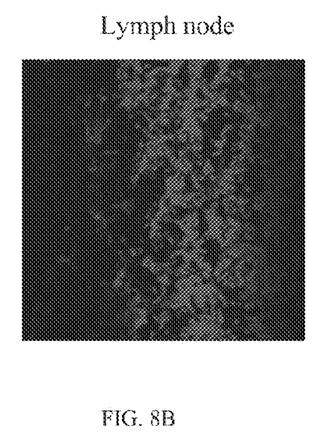
Figure 8C:
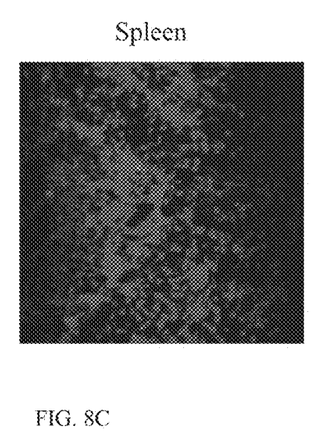
Figure 9A:
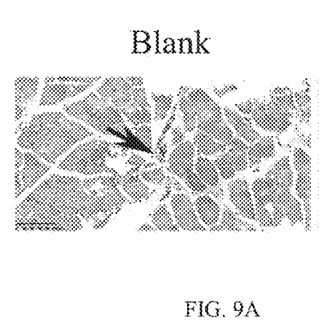
FIGS. 9A-9C show pathological changes of local tissues in animals injected with the VLS experimental vaccine of Example 1 of the present disclosure.
Figure 9B:
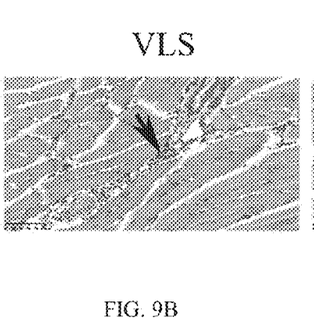
Figure 9C:
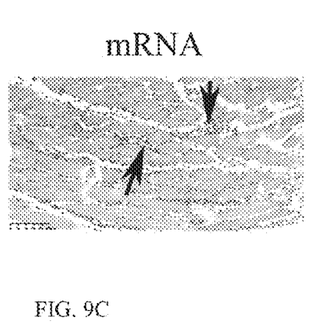

Results showed that the fluorescent protein was mainly expressed in local and surrounding lymph node tissues of injection, and no fluorescence was observed in major organs such as heart, liver, lung, kidney, brain, and spine (FIGS. 8A-8C, Table 2). This was also demonstrated by specific q-RT-PCR test results of relevant organs and tissues after $ACE2^{+/+}$ mice were immunized with the VLS experimental vaccine that included a designed S1 gene mRNA and an S1 protein embedded on a surface of a lipid membrane (Table 2).

TABLE 2

Distribution of the immune VLS experimental vaccine in tissues and organs

| | mRNA | | | | VLS | | | |
|---|---|---|---|---|---|---|---|---|
| | 1 | 3 | 5 | 7 | 1 | 3 | 5 | 7 |
| Heart | − | − | − | − | − | − | − | − |
| Liver | − | − | − | − | − | − | − | − |
| Spleen | + | + | + | + | + | + | + | + |
| Lung | − | − | − | − | − | − | ± | − |
| Kidney | − | − | − | − | − | − | − | − |
| Brain | − | − | − | − | − | − | − | − |
| Lymph node | + | + | + | ± | + | + | + | + |
| Muscle (immune site) | + | + | + | − | + | + | + | − |

Clinical observations of mRNA vaccines already in use have shown that side reactions caused by a lipid delivery system are usually inflammatory responses of local tissues. Therefore, histopathological changes of local tissues in animals injected with the VLS experimental vaccine were observed, especially the local inflammatory responses.

Results showed that the VLS experimental vaccine caused a mild inflammatory response and an aggregation degree of inflammatory cells similar to that of the mRNA vaccine currently in use (FIGS. 8A-8C).

The above safety observations showed that the VLS experimental vaccine is safe and reliable in current animal experiments.

Finally, it should be noted that the above preferred embodiments are merely intended to illustrate rather than limit the technical solutions of the present disclosure. Although the present disclosure has been described in detail through the above preferred embodiments, those skilled in the art should appreciate that various changes may be made to the present disclosure in the form and detail without departing from the scope defined by the claims of the present disclosure.

What is claimed is:

1. A virus-like structure (VLS) vaccine, comprising a lipid nanoparticle (LNP), wherein the LNP comprises:
    a first cationic lipid of ((2-(2-hydroxyethoxy)ethyl) azanediyl)bis(hexane-6,1-diyl)bis(2-hexyldecanoate) (DHA-1),
    a second cationic lipid of (2,3-dioleoyl-propyl)-trimethylammonium-chloride (DOTAP),
    a phospholipid of 1,2-dioleoyl-SN-glycero-3-phosphocholine (DOPC), and
    a polyethylene glycol (PEG)-lipid of methoxypoly(ethylene glycol)-N-tetradecyltetradecanamide-2K (mPEG-DTA-1-2K); and wherein
    the LNP encapsulates a non-self-replicating mRNA encoding a SARS-CoV-2 membrane spike (S1) protein; and wherein a surface of the LNP comprises an S1 antigen protein bound to the surface.

2. The VLS vaccine according to claim 1, wherein
    the LNP encapsulates a non-self-replicating mRNA encoding an S1 protein of a SARS-CoV-2 Omicron virus strain; and wherein
    a surface of the LNP comprises an S1 antigen protein bound to the surface, wherein the S1 antigen protein is encoded by an S1 gene expressed in a Chinese hamster ovary (CHO) cell.

3. A preparation method of the VLS vaccine according to claim 2, comprising the following steps:
    (1) mixing the DHA-1, the DOTAP, the DOPC, and the mPEG-DTA-1-2K dissolved in absolute ethanol according to a molar ratio of (10-13):(27-29):(56-59): (1.6-1.9) to obtain a mixed solution; and
    diluting the mRNA with 10 mM NaAc, and 0.0001% (w/v, trehalose (buffer D) to obtain a diluted mRNA;
    (2) encapsulating the diluted mRNA with the mixed solution obtained in step (1) by a microfluidic device to produce an mRNA-LNP system;
    (3) diluting the mRNA-LNP system obtained in step (2) with buffer D in a volume 30 times a volume of the mRNA-LNP system, and subjecting a resulting diluted system to an ultrafiltration (UF) concentration with a 100 kDa UF membrane to obtain a filtered mRNA-LNP system;
    (4) using 500 mM acetic acid (HA) to adjust a pH of the filtered mRNA-LNP system to 6.2 to 6.8 to obtain an adjusted mRNA-LNP system;
    (5) adding the S1 antigen protein expressed in the CHO cell and purified by chromatography to buffer D with a pH of 6.2 to 6.8 to prepare a protein preparation solution system; and
    (6) mixing the adjusted mRNA-LNP system obtained in step (4) with the protein preparation solution system obtained in step (5), and subjecting a resulting mixed system to a rotary-mixing at room temperature for 30 min and then staying overnight at 4° C. to obtain a stock solution for the vaccine.

4. The VLS vaccine according to claim 1, wherein the DHA-1, the DOTAP, the DOPC, and the mPEG-DTA-1-2K are in a molar ratio of (10-13):(27-29):(56-59):(1.6-1.9).

* * * * *